United States Patent [19]
White et al.

[11] Patent Number: 5,860,969
[45] Date of Patent: Jan. 19, 1999

[54] VERSION ADJUSTMENT INSTRUMENT FOR MODULAR FEMORAL COMPONENTS AND METHOD OF USING SAME

[75] Inventors: John White, Winona Lake; Roy Wiley, Warsaw, both of Ind.

[73] Assignee: Biomet, Inc., Warsaw, Ind.

[21] Appl. No.: 835,848

[22] Filed: Apr. 30, 1997

[51] Int. Cl.⁶ .................................. A61F 2/32; A61F 5/00
[52] U.S. Cl. .............................................................. 623/22
[58] Field of Search .................................. 623/16, 18, 23; 606/53, 86, 87, 91, 96, 97, 102

[56] References Cited

U.S. PATENT DOCUMENTS

| | | |
|---|---|---|
| 2,724,187 | 11/1955 | Barzilai . |
| 2,737,724 | 3/1956 | Herz . |
| 2,775,040 | 12/1956 | Leff . |
| 3,229,372 | 1/1966 | Quashnock et al. . |
| 3,358,373 | 12/1967 | Martin . |
| 4,358,897 | 11/1982 | Hornbeck . |
| 4,627,425 | 12/1986 | Reese . |
| 5,002,581 | 3/1991 | Paxson et al. . |
| 5,038,489 | 8/1991 | Muehlenbein . |
| 5,080,685 | 1/1992 | Bolesky et al. . |
| 5,108,396 | 4/1992 | Lackey et al. . |
| 5,141,512 | 8/1992 | Farmer et al. . |
| 5,181,928 | 1/1993 | Bolesky et al. . |
| 5,194,066 | 3/1993 | Van Zile . |
| 5,286,260 | 2/1994 | Bolelsky et al. . |
| 5,370,706 | 12/1994 | Bolesky et al. . |

OTHER PUBLICATIONS

Brochure entitled, "The S–Rom® Total Hip System—Addresses the Issues" by Joint Medical Products Corporation, 1993, 19 pages.

Brochure entitled, "Mallory Head® Hip—Program Modular Calcar Revision Series" by BIOMET® Inc., 1995, 36 pages.
Brochure entitled, "Infinity™ Modular Hip Design", by Dow Corning Wright, 1990, 15 pages.
Brochure entitled, "Infinity™ Modular Hip Design Surgical Technique", by Dow Corning Wright, 1990, 12 pages.
Brochure entitled, "The S–Rom™ Tri–Version™ Femoral Stem System using ZT™ Graduated Proximal Sleeves Surgical Technique" by Joint Medical Products Corporation, 1991, 16 pages.
Brochure entitled, "The S–Rom™ Total Hip System†" by Joint Medical Products Corporation, 1990, 8 pages.

*Primary Examiner*—David J. Isabella
*Attorney, Agent, or Firm*—Michael McNeil

[57] ABSTRACT

A version adjustment instrument is utilized with modular femoral components, including a modular stem component having a coronal slot and/or a bowed portion and a modular body component attachable to the modular stem component in a substantially fixed orientation relative to the coronal slot or bowed portion. The instrument includes a base with a face surface having a plurality of adjacent angle markings. A body component support has a first coupler formed to engage the modular body component in a substantially fixed orientation relative to the body component support. A stem locator has a second coupler formed to engage one of either the coronal slot or bowed portion (if any) of the modular stem component in a substantially fixed orientation relative to the stem locator. One of the body component support or the stem locator is connected to the base at a position away from the face surface in a substantially fixed orientation relative to the angle markings. The other of the two is rotatably mounted to the base about an axis of rotation and includes a pointer projecting away from the axis of rotation with a portion adjacent the angle markings.

20 Claims, 5 Drawing Sheets

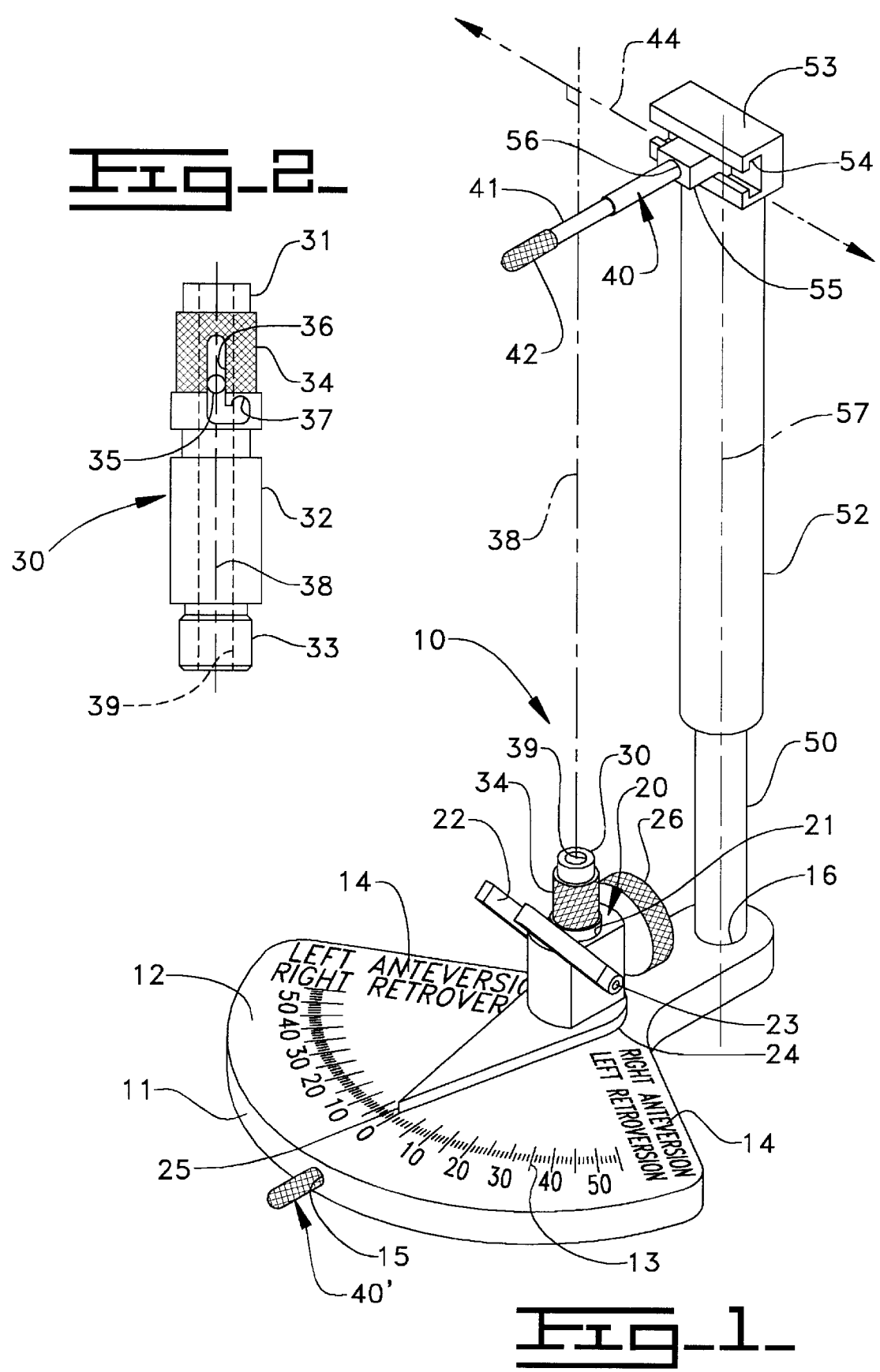

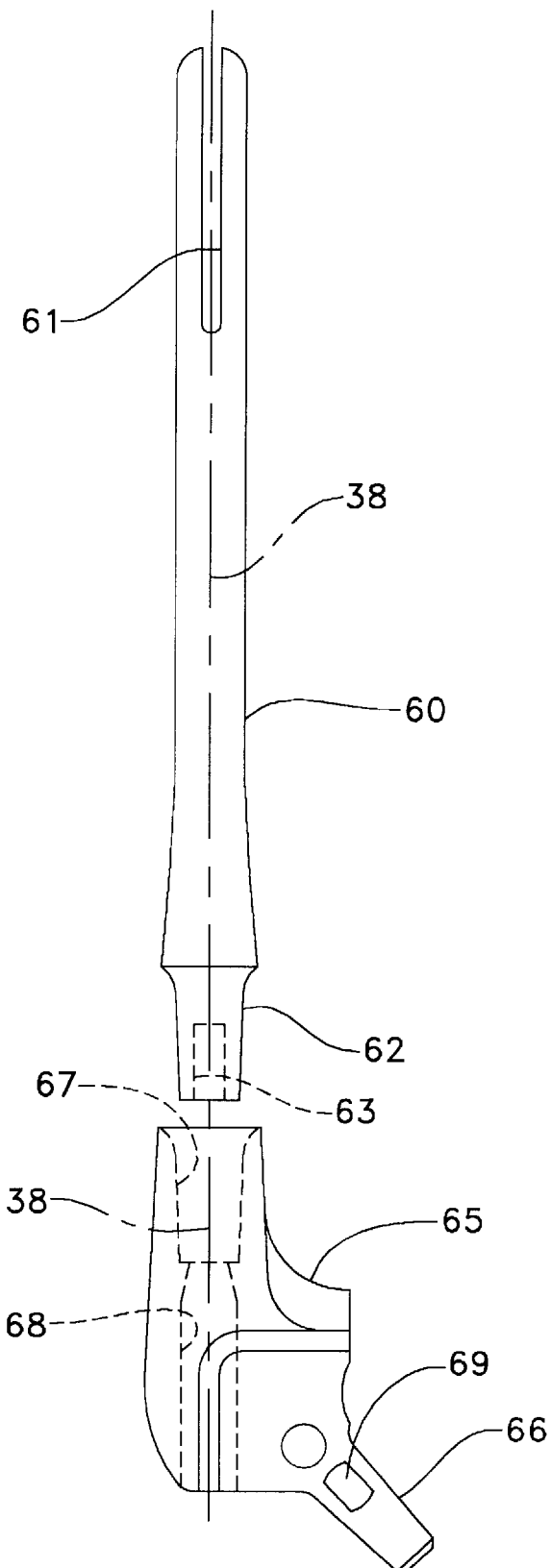
Fig_3_

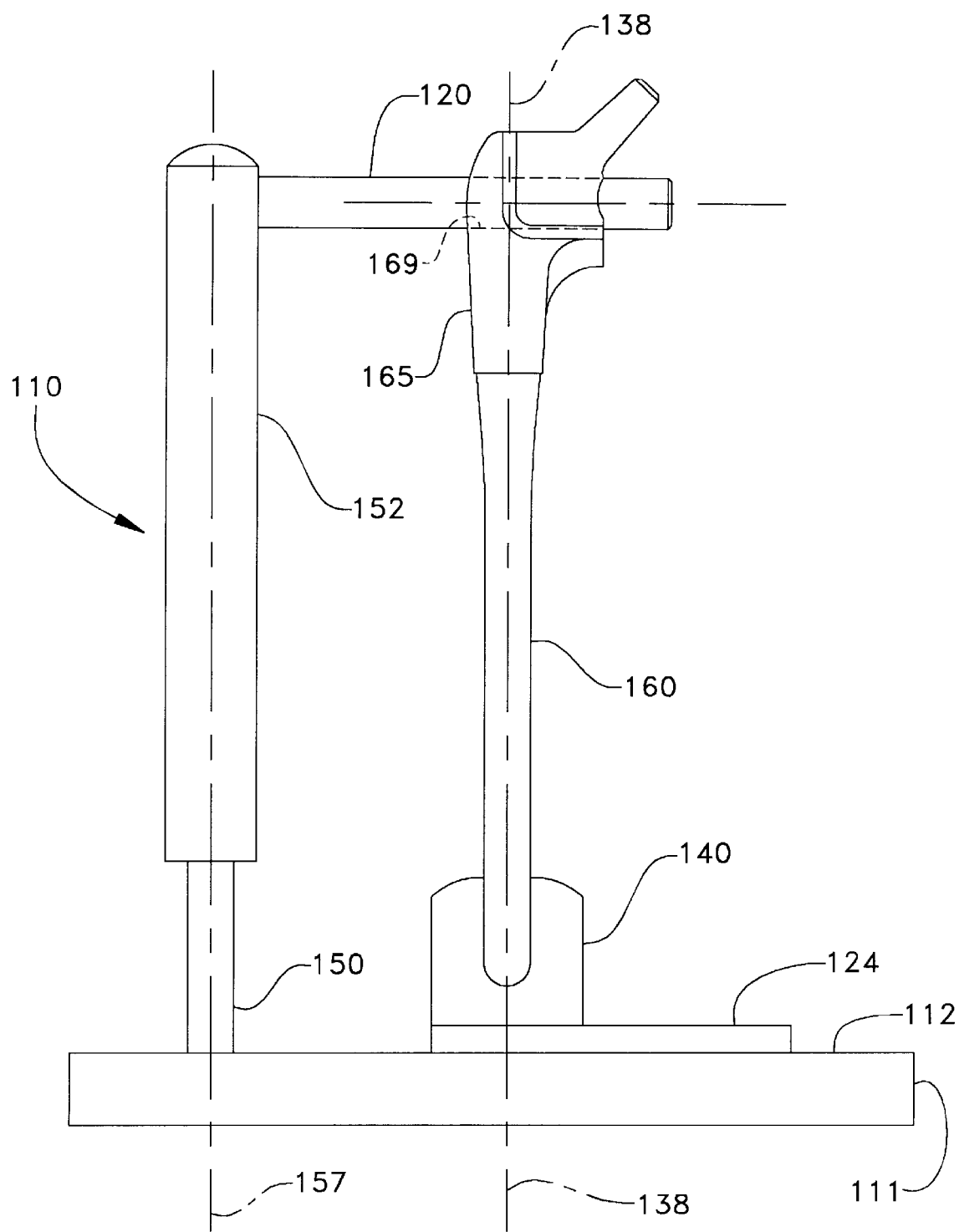

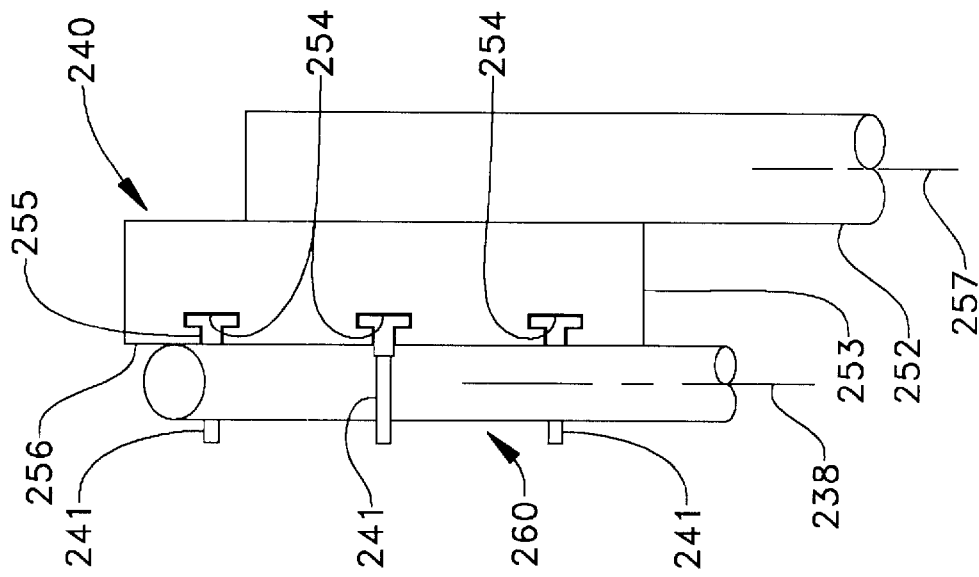
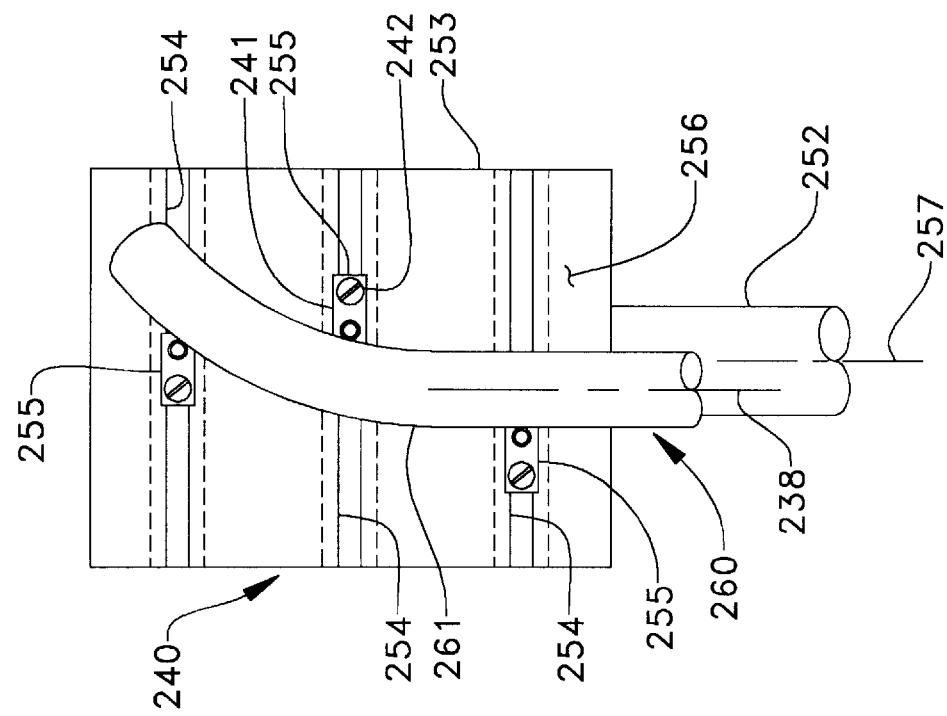

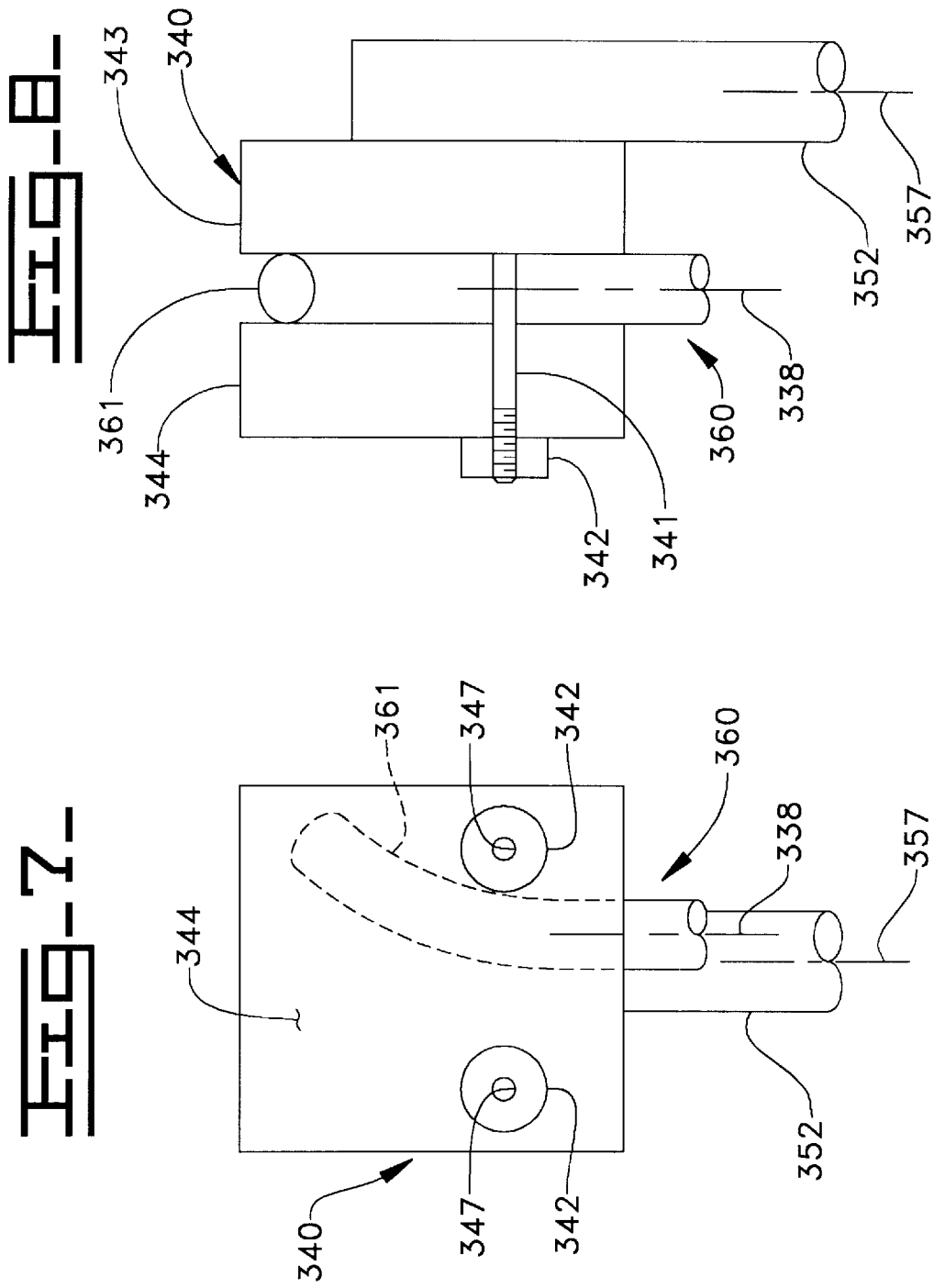

5,860,969

VERSION ADJUSTMENT INSTRUMENT FOR MODULAR FEMORAL COMPONENTS AND METHOD OF USING SAME

TECHNICAL FIELD

This invention relates generally to modular femoral prostheses, and more particularly to a version adjustment instrument for accurately arranging modular femoral components in a desired orientation before implantation.

BACKGROUND ART

Various modular prostheses have heretofore been designed to replace one or both ball and socket hip joints. Generally, a body component is connected to a stem component, which is embedded in the intramedullary canal of the proximal femur for hip reconstruction. An artificial ball is attached to the body component and received in a socket portion, which is attached to the hip bone. The recognized advantage of modular components lies in the ability to custom fit the prosthesis by having available a multitude of different sized and shaped body and stem components, all of which are attachable to one another. One such example includes the modular body revision series manufactured by Biomet, Inc. and sold under the trade name Mallory-Head® Hip Program. In that product line, three different stem lengths are available in five different diameters, and three differently shaped body components are each available in five different sizes. Thus, in that product line physicians have the ability to assemble two hundred and twenty-five different prostheses utilizing different combinations of the available components.

In addition to having the ability to assemble literally hundreds of different prostheses from available components, further variations are available by the fact that the modular components can be assembled to one another in any angular orientation. While this angular orientation is generally not important in those cases where the stem portion is straight and does not include a coronal slot, it is critically important in those cases where the stem includes a coronal slot and/or includes a bowed portion to match the bow in the bone being replaced. The coronal slot orientation reduces bending stress along the coronal plane, and therefore its orientation is of critical importance to the long-term success of an implanted prosthesis in preventing fracture after implantation.

In many modular component systems, provisional components are positioned at the implantation site in order to precisely size and determine the desired angular orientation for the actual prosthesis. While the use of provisional components allows the physician to accurately size the modular prosthesis, accurately transferring the angular orientation of the components from a provisional implant to the actual modular prosthesis has been somewhat more problematic. One known method for transferring the angular orientation of the provisional implant to the actual prosthesis is described in U.S. Pat. No. 5,135,529 to Paxson, et al. In this patent, angular markings on the implants themselves are aligned to correspond to a vertical line etched on the stem component. However, because the angular markings are rather crude and because they are located a relatively short distance from the axis of rotation, the procedure described in Paxson, et al. can still result in an angular deviation from a desired orientation as much as plus or minus 10°. Other known systems simply rely only upon the physician's estimate, and consequently result in even cruder settings of the angular orientation between the modular components. Thus, while modular components have the ability to provide a precise size fitting, there remains significant room for improvement in setting the angular orientation of the components relative to one another in order to provide an even better precisely matched fit for the implantation of a prosthesis in an individual patient.

SUMMARY OF THE INVENTION

In responding to the need to provide a more accurate angular orientation settings for modular femoral components, the present invention provides a modular adjustment instrument that includes a modular stem component having either a coronal slot, a bowed portion, or both, and a modular body component attachable to the modular stem component in a substantially fixed orientation relative to either the coronal slot or bowed portion. The instrument includes a base with a face surface having a plurality of adjacent angle markings. A body component support has a first coupler formed to engage the modular body component in a substantially fixed orientation relative to the body component support. A stem locator has as second coupler formed to engage one of either the coronal slot or bowed portion of the modular stem component in a substantially fixed orientation relative to the stem locator. One of the body component support or the slot locator is connected to the base at a position away from the face surface in a substantially fixed orientation relative to the angle markings. The other of the two is rotatably mounted to the base about an axis of rotation and includes a pointer projecting away from the axis of rotation with a portion adjacent the angle markings.

In another embodiment of the present invention, a method of assembling a modular femoral prosthesis includes the steps of attaching a provisional modular stem component having either a first coronal slot, a first bowed portion, or both to a provisional modular body component in a desired orientation to make a provisional prosthesis. The provisional prosthesis is then mounted on a version adjustment instrument having a base with a face surface with a plurality of adjacent angle markings, a body component support with a first coupler formed to engage a modular body component, and a stem locator with a second coupler formed to engage one of either the coronal slot or bowed portion of a modular stem component. The version adjustment instrument is then adjusted into a configuration corresponding to the desired orientation. The provisional prosthesis is then removed from the version adjustment instrument. Next, a loosely assembled modular femoral prosthesis is mounted on the version adjustment instrument. The modular stem prosthesis is then oriented relative to the modular body prosthesis in the desired orientation using the version adjustment instrument. Finally, the modular stem prosthesis is secured to the modular body prosthesis in the desired orientation.

In still another embodiment of the present invention, a set for the assembly of a modular bone joint prosthesis for the replacement of a body portion, a stem portion and adjacent portions of a bone includes a plurality of provisional modular stem components each having a provisional coronal slot, a bowed portion, or both. Also included are a plurality of provisional modular body components, each of which are attachable to any of the modular stem components in a substantially fixed orientation relative to either the provisional coronal slot or provisional bowed portion. A plurality of modular stem prostheses each has a prosthesis coronal slot and/or a prosthesis bowed portion, and a plurality of modular body prostheses are each attachable to any of the modular stem prostheses in a substantially fixed orientation relative to one of either the prosthesis coronal slot or prosthesis bowed portion. A version adjustment instrument includes a base with a face surface having a plurality of adjacent angle markings; a body component support having a first coupler formed to engage any of the provisional modular body components or the modular body prostheses in a substantially fixed orientation relative to the body component support; and a stem locator with a second coupler formed to engage any of the provisional coronal slots or provisional bowed portions of the provisional modular stem components or, the prosthesis coronal slots or prosthesis bowed portions of the modular stem prostheses in a substantially fixed orientation relative to the stem locator.

One object of the present invention is to allow physicians to improve the accuracy of angular orientation settings for modular femoral prostheses.

Another object of the present invention is to allow physicians to accurately measure the anteversion or retroversion angle for a modular femoral prosthesis.

BRIEF DESCRIPTION OF THE DRAWINGS

FIG. 1 is an isometric view of a version adjustment instrument according to the present invention.

FIG. 2 is a side elevational view of a spindle assembly for the version adjustment instrument shown in FIG. 1.

FIG. 3 is a sample unassembled modular femoral prosthesis for use with the version adjustment instrument of the present invention.

FIG. 4 is a side elevational view of a version adjustment instrument according to another embodiment of the present invention.

FIG. 5 is a partial front view of a version adjustment instrument according to still another embodiment of the present invention.

FIG. 6 is a partial side view of the version adjustment instrument of FIG. 5.

FIG. 7 is a partial front view of a version adjustment instrument according to another embodiment of the present invention.

FIG. 8 is a partial side view of the version adjustment instrument of FIG. 7.

DETAILED DESCRIPTION OF THE PREFERRED EMBODIMENTS

Referring now to FIG. 1, a version adjustment instrument 10 includes a base 11 with a face surface 12 that is formed from a suitable substantially rigid material. Face surface 12 is etched or marked to include a plurality of adjacent angle markings 13, which are preferably set in increments of about 1°. Face surface 12 is also marked to indicate whether an angle is anteversion or retroversion, which depends on whether the prosthesis will replace a portion of the left or right femur. The zero angle marking in the center of face surface 12 indicates a neutral setting that is neither retroversion or anteversion.

Referring also to FIG. 2, a spindle 30 includes an upper cylindrical portion 31, a middle cylindrical portion 32 and a lower cylindrical portion 33. Spindle 30 is fixedly mounted in base 11 by lower cylindrical portion 33 being received in a bore, which is not shown, in base 11. Spindle 30 includes a central axis 38 which is oriented substantially perpendicular to face surface 12 of base 11. A central bore 39 runs the entire length of spindle 30, and allows a fixation tool, such as an Allen head screwdriver, to pass through spindle and into a modular body component mounted on upper cylindrical portion 31. Spindle 30 also includes a knurled sleeve 34 which is slidably mounted on upper cylindrical portion 31 and moveable between an upper position and a lower position. A pin 35 is mounted in upper cylindrical portion 31 and rides within a slot 36 machined through the side of knurled sleeve 34. A notch 37 in slot 36 allows knurled sleeve 34 to be fixed in its upper position. By the use of upper cylindrical portion 31 or knurled sleeve 34, two different diameters can be presented to a modular body component mounted on the top of spindle 30. In some modular femoral component sets, the provisional body components have a smaller diameter entry hole than their counterpart modular body prosthesis. The knurled sleeve 34 of spindle 30 allows the version adjustment instrument to accommodate both.

Spindle 30 forms part of a body component support 20, which also includes a pointer assembly 21. The pointer assembly includes a bore therethrough that is rotatably received on middle cylindrical portion 32 of spindle 30, and is rotatable about axis of rotation 38. Pointer assembly 21 is supported on face surface 12 by a pointer 24 having a tip 25 that is positioned adjacent angle markings 13 on face surface 12. A set screw 26 allows pointer assembly 21 to be fixed at any angular orientation about axis of rotation 38 of spindle 30. A fork 22 is pivotably mounted on pointer assembly 21 and pivotable about an axis 23, which is substantially parallel to face surface 12. A hidden torsional spring biases fork 22 upward as shown. Fork 22 acts as a coupler to engage a pair of corresponding planar surfaces or the male taper machined in the provisional modular body components, as well as a corresponding pair of planar surfaces or male taper machined on the modular body prostheses. In this way, a modular body component is supported by body component support 20 in a fixed angular orientation relative to tip 25 of pointer assembly 21. Fork 22 is preferably made from a suitable semi-rigid plastic; the remaining portions of version adjustment instrument 10 are preferably made from a suitable metallic alloy.

A rigid rod 50 has a portion received in a bore 16 in base 11 such that it is attached to and projects away from base 11 in a parallel direction 57 that is substantially parallel to axis of rotation 38. A telescopic extension 52 is slidably mounted on rod 50 and moveable up and down in parallel direction 57. A pin and slot arrangement, which cannot be seen, between telescopic extension 52 and rod 50 prevents the two from rotating with respect to one another. A head portion 53 is fixably attached to the top of telescopic extension 52, and includes a keyed slot 54 across its complete width. A T-slide 55 is slidably mounted in keyed slot 54 and movable laterally in a direction 44, which is substantially perpendicular to both axis of rotation 38 and parallel direction 57.

T-slide 55 includes a threaded bore 56, which receives a counterpart male threaded portion of a stem locator 40. Stem locator 40 is attached to T-slide 55 by rotating its threaded end into threaded bore 56 by gripping knurled end 42. A central cylindrical portion 41 of stem locator 40 is sized to be received in the coronal slot of a modular stem component, and acts as a coupler. In other words, when cylindrical portion 41 is received in the coronal slot of a modular stem component, the two are fixed in their angular orientation relative to one another. The ability to move T-slide 55 from side to side is useful in accommodating those modular stem components that also have a bowed portion in addition to a coronal slot. In order to accommodate different sized coronal slots, a second stem locator 40' with a different cylindrical portion diameter is removably mounted in a threaded bore 15 in base 11. Thus, stem locator 40 and 40' can be interchanged depending upon the width of the coronal slot of the particular modular stem component being utilized.

Version adjustment instrument 10 is intended to be used as a portion of the set that would also include a plurality of provisional modular stem components each having a provisional coronal slot and/or a provisional bowed portion, and a plurality of provisional modular body components (and rasp/provisionals) which are each attachable to any of the modular stem components in a substantially fixed orientation relative to the provisional coronal slot. Also included in such a set would be a plurality of modular stem prostheses each having a prosthesis coronal slot and/or prosthesis bowed portion, and a plurality of modular body prostheses each being attachable to any of the modular stem prostheses in a substantially fixed orientation relative to the prosthesis coronal slot or prosthesis bowed portion. Each of the provisional modular stem components would have a counterpart modular stem prostheses with a substantially identical size and shape. Likewise each modular body component would have a counterpart modular body prosthesis. In this way, the physician can arrive at a desired prosthesis size and orientation utilizing the provisional components.

When in use, the physician determines the size of the final implantable prosthesis components by utilizing a variety of provisional components or rasp/provisional components in a manner known in the art. When the provisional components or rasp/provisional components are properly sized, the physician fixes the provisional body component in a desired angular orientation relative to the coronal slot and/or bowed portion of the provisional stem component. FIG. 3 shows a sample unassembled femoral component which could represent either a provisional or prosthesis. In most cases, the modular stem component 60 will include a coronal slot 61 on one end (or a bowed portion without a coronal slot) and an extension 62 that is sized to be received in a counterpart bore 67 in a modular body component 65. A screw access bore 68 allows a fastener screw (not shown) to fixably attach stem component 60 to body component 65 such that coronal slot 61 is fixed in any desired angular orientation about axis of rotation 38 relative to neck portion 66 of body component 65. Body component 65 is machined to include a pair of parallel planar surfaces 69 that are engaged by fork 22 of pointer assembly 20 when spindle 30 is received in screw access bore 68. The fork can also engage the male taper 66.

After the physician has chosen the provisional components, they are fixed in a desired angular orientation, usually at the implantation site of the patient. In other cases, a desired anteversion or retroversion angle can be determined based upon other factors known in the art, such as to improve a mismatch between the left and right femurs of a particular patient, or to correct a pathologic abnormality.

With the provisional prosthesis secured in a desired orientation, it is mounted on the version adjustment instrument by inserting its coronal slot into stem locator 40 of the instrument. This is usually done by lifting telescoping extension 52 a sufficient distance so that engagement of the stem portion to the stem locator is not interfered with by the body component support 20 below. Next, the pointer assembly 21 is rotated just below the provisional or rasp body component until fork 22 can engage planer surfaces 69 on the modular body component 65. This activity requires rotation of pointer assembly 21 about axis of rotation 38 until the tip 25 of pointer 24 points toward an angle that corresponds to the desired anteversion or retroversion angle of the provisional prosthesis. Set screw 26 is then utilized to fix version adjustment instrument 10 in the configuration corresponding to the desired orientation of the provisional prosthesis. The provisional prosthesis is then removed from version adjustment instrument 10 by again lifting telescopic extension 52 and pulling the provisional prosthesis away from stem locator 40.

Next, a loosely assembled modular femoral prosthesis utilizing components that correspond in size and shape to the provisional components is mounted on the version adjustment instrument. When the coronal slot of the modular stem prosthesis has engaged the stem locator 40 and the fork 22 has engaged the modular body component, the modular femoral prosthesis is tentatively in an orientation corresponding to the desired orientation of the provisional components. In order to fix the components in this desired orientation, a fastening tool, such as an Allen head screwdriver, is advanced up through bore 39 in spindle 30 until it engages the fastening screw loosely attached inside of modular body component 65. The modular stem prosthesis and modular body prosthesis are then fixed in the desired angular orientation by advancing the attachment screw in a manner known in the art. The modular femoral prosthesis is then removed from version adjustment instrument 10 and implanted in the patient in a conventional manner.

Referring now to FIG. 4, another embodiment of a version adjustment instrument 110 is shown illustrated. This embodiment is similar to the previous embodiment except that the pointer 124 is attached to the stem locator 140 which is rotatable relative to the base 111, instead of being attached to the body component support, as in the previous embodiment. Thus, in this embodiment the body component support 120 is located at a position away from face surface 112 of the base 111 in a fixed orientation relative to the angle markings, whereas in the previous embodiment the stem locator was positioned away from the base at a fixed orientation relative to the angle markings. The principles of utilizing both devices is the same in that one component is rotated relative to the other until a desired orientation is achieved. In this embodiment, modular body component 120 includes a rod attached on one end to a telescopic extension 152. The horizontal rod of body component support 120 is received in a bolt hole 169 in a modular body component. In this embodiment, stem locator 140 is simply a thin upward projection that is received in the coronal slot of a modular stem component 160. This embodiment is similar to the earlier embodiment in that it includes an upright rod 150 that allows telescopic extension to move up and down along a parallel direction 157 that is parallel to axis of rotation 138.

Referring now to FIGS. 5 and 6, a stem locator 240 is shown in use with a prosthesis 260 having a bowed portion 261, but no coronal slot. In this case, telescoping stem 252 and the portions there above would be substituted in place of the telescoping stem 52 shown in FIG. 1, but the remaining features shown in FIG. 1 would be the same. In this case, a mounting block 253 is attached to telescoping stem 52 and includes three guide slots 254 machined across its entire width. A T-slide 255 is slidably received in each of the different guide slots 254. Each T-slide includes a pin 241 that projects perpendicularly away from a plane 256 defined by block 253. Each T-slide 255 also includes a set or thumb screw 242 that allow the slide to be fixed in place. When in use, the individual T-slides 255 are slid so that pins 241 are in contact with the outer surface of prosthesis 260. They are then fixed into place with set screws 242. The prosthesis 260 is then held in place against plane 256 so that it cannot rotate with respect to its stem axis 238 or telescope axis 257. Thus, those skilled in the art will appreciate that this stem coupler 240 can be utilized in those cases where the stem has a bowed portion 261, but no coronal slot.

Referring now to FIGS. 7 and 8, a stem locator 340 is shown in use with a prosthesis 360 having a bowed portion 361, but no coronal slot. This embodiment is an alternative to that shown in FIGS. 5 and 6. In this case, telescoping stem 352 and the portions there above would be substituted in place of telescoping stem 52 shown in FIG. 1, but the remaining features shown in FIG. 1 would be the same. Stem locator 340 includes a mounting block 343 attached to telescoping stem 352 and includes a pair of threaded pins 341 attached thereto and protruding away in a perpendicular direction as shown. A holding block 344 has a pair of spaced apart bores 347 that receive the ends of pins 341. A pair of nuts 342 thread onto the ends of pins 341 so that the bowed end 361 can be pinched between holding block 344 and mounting block 343. When in the position shown, prosthesis 360 is fixed into place and cannot rotate with respect to its stem axis 338 or telescope axis 357. Thus, those skilled in the art will appreciate that this stem coupler 340 can be utilized in those cases where the stem has a bowed portion 361, but no coronal slot.

It should be understood that the above embodiments are intended for illustrative purposes only, and are not intended to limit the scope of the present invention in any way. For instance, the version adjustment instrument of the present invention can be used without provisional components in those cases where the physician wishes the final prosthesis to have a certain anteversion or retroversion angle, which may be pre-set on the instrument using the set screw. Also, the present invention contemplates a provisional or prosthesis stem but no coronal slot. In such a case, the stem locator would have to be modified as per FIGS. 5 and 6 to engage the bowed portion in a fixed orientation. Other various modifications can be made by those skilled in the art to the structure of the version adjustment instrument of the present invention and its method of use without departing from the spirit and scope of the invention as defined in the appended claims.

We claim:

1. A version adjustment instrument for modular femoral components comprising:
    a modular stem component having a stem orientation defined by at least one of a coronal slot and a bowed portion;
    a modular body component attachable to said modular stem component in a substantially fixed orientation relative to said stem orientation;
    a base with a face surface having a plurality of adjacent angle markings;
    a body component support having a first coupler formed to engage said modular body component in a substantially fixed orientation relative to said body component support;
    a stem locator having a second coupler formed to engage one of either said coronal slot or said bowed portion of said modular stem component in a substantially fixed orientation relative to said stem orientation;
    one of said body component support or said stem locator being connected to said base at a position away from said face surface in a substantially fixed orientation relative to said angle markings, and the other being rotatably mounted to said base about an axis of rotation and including a pointer projecting away from said axis of rotation with a portion adjacent said angle markings.

2. The version adjustment instrument of claim 1 wherein said stem locator is rotatably attached to said base about said axis of rotation, and includes said pointer.

3. The version adjustment instrument of claim 1 wherein said body component support includes a spindle attached to and projecting away from said base along said axis of rotation, and a pointer assembly rotatably mounted on said spindle and having said first coupler and said pointer attached to said pointer assembly.

4. The version adjustment instrument of claim 3 further comprising:
    a rod attached to and projecting away from said base in a parallel direction substantially parallel to said axis of rotation; and
    a telescopic extension slidably mounted on said rod and movable in said parallel direction; and
    said stem locator being mounted on said telescopic extension.

5. The version adjustment instrument of claim 4 wherein said stem locator is slidably mounted on said telescopic extension and being laterally movable perpendicular to said axis of rotation.

6. The version adjustment instrument of claim 4 wherein said first coupler is a fork pivotably attached to said pointer assembly and pivotable about a pivot axis substantially perpendicular to said axis of rotation; and
    said second coupler of said stem locator includes a portion sized to be received in said coronal slot of said modular stem component.

7. The version adjustment instrument of claim 4 wherein said pointer assembly includes a set screw for fixing the orientation of said pointer assembly relative to said angle markings about said axis of rotation.

8. The version adjustment instrument of claim 4 wherein said body component support includes a sleeve with a knurled outer surface slidably mounted on said spindle and movable along said parallel direction between an upper position and a lower position.

9. The version adjustment instrument of claim 3 wherein said spindle includes a bore therethrough that opens beneath said base and is sized to receive a fixation tool therethrough.

10. The version adjustment instrument of claim 1 wherein said angle markings are in increments of less than 10°.

11. The version adjustment instrument of claim 10 wherein said angle markings are in increments of about 1°.

12. The version adjustment instrument of claim 1 wherein said face surface includes an indicator marking indicating whether an angle is anteversion or retroversion.

13. A method of assembling a modular femoral prosthesis comprising the steps of:
    adjusting a version adjustment instrument into a configuration corresponding to a desired orientation, said version adjustment instrument having a base with a face surface with a plurality of adjacent angle markings, a body component support with a first coupler formed to engage a modular body component and a stem locator having a second coupler formed to engage one of either a coronal slot or a bowed portion of a modular stem component;
    mounting a loosely assembled modular femoral prosthesis that includes a modular stem prosthesis with at least one of a prosthesis coronal slot and a prosthesis bowed portion, and a modular body prosthesis on said version adjustment instrument;
    orienting said modular stem prosthesis relative to said modular body prosthesis in said desired orientation using said version adjustment instrument; and
    securing said modular stem prosthesis to said modular body prosthesis in said desired orientation.

14. The method of claim 13 further comprising the steps of:

attaching a provisional modular stem component having at least one of a provisional coronal slot and a provisional bowed portion to a provisional modular body component in said desired orientation to make a provisional prosthesis;

mounting said provisional prosthesis on said version adjustment instrument; and removing said provisional prosthesis from said version adjustment instrument after said adjusting step.

15. The method of claim 14 wherein said body component support includes a spindle attached to said base, and a pointer assembly rotatably mounted on said spindle about an axis of rotation that includes said first coupler; and said step of mounting said provisional prosthesis includes the steps of engaging one of either said provisional coronal slot or said provisional bowed portion to said second coupler of said stem locator and rotating said pointer assembly until said first coupler on said pointer assembly engages said provisional modular body component.

16. The method of claim 13 wherein said step of mounting a loosely assembled modular femoral prosthesis includes the steps of engaging one of either said prosthesis coronal slot or said provisional bowed portion with said second coupler of said stem locator and rotating said modular body prosthesis relative to said modular stem prosthesis until said first coupler is positioned to engage said modular body prosthesis.

17. The method of claim 13 further comprising the step of fixing said version adjustment instrument in said configuration after said step of adjusting said version adjustment instrument.

18. The method of claim 15 wherein said adjusting step includes a steps of:

measuring said desired orientation using said version adjustment instrument; and determining whether said desired orientation is anteversion or retroversion.

19. A set for the assembly of a modular femoral prosthesis for the replacement of a body portion, a stem portion and adjacent portions of a femur, the set comprising:

a plurality of provisional modular stem components each having at least one of a provisional coronal slot and a provisional bowed portion;

a plurality of provisional modular body components each being attachable to any of said provisional modular stem components in a substantially fixed orientation relative to at least one of said provisional coronal slot and said provisional bowed portion;

a plurality of modular stem prostheses each having at least one of a prosthesis coronal slot and a prosthesis bowed portion;

a plurality of modular body prostheses each being attachable to any of said modular stem prostheses in a substantially fixed orientation relative to said prosthesis coronal slot or said prosthesis bowed portion; and a version adjustment instrument that includes a base with a face surface having a plurality of adjacent angle markings; a body component support having a first coupler formed to engage any of said provisional modular body components or said modular body prostheses in a substantially fixed orientation relative to said body component support; and a stem locator having a second coupler formed to engage any of one of either said provisional coronal slots or said provisional bowed portions of said provisional modular stem components or one of either said prosthesis coronal slots or said prosthesis bowed portions of said modular stem prostheses in a substantially fixed orientation relative to said stem locator.

20. The set of claim 19 wherein one of said body component support or said stem locator is connected to said base at a position away from said face surface in a substantially fixed orientation relative to said angle markings, and the other being rotatably mounted to said base about an axis of rotation and including a pointer projecting away from said axis of rotation with a portion adjacent said angle markings.

* * * * *